United States Patent [19]

Van Iten et al.

[11] Patent Number: 4,886,632
[45] Date of Patent: Dec. 12, 1989

[54] METHOD OF PERFORATING A NONWOVEN WEB AND USE OF THE WEB AS A COVER FOR A FEMININE PAD

[75] Inventors: Thomas P. Van Iten, Neenah; Howard A. Whitehead, Appleton; Julie A. Schindel, Oshkosh, all of Wis.

[73] Assignee: Kimberly-Clark Corporation, Neenah, Wis.

[21] Appl. No.: 231,752

[22] Filed: Aug. 11, 1988

Related U.S. Application Data

[60] Continuation-in-part of Ser. No. 32,154, Mar. 27, 1987, abandoned, which is a division of Ser. No. 774,252, Sep. 9, 1985, abandoned.

[51] Int. Cl.[4] .................. B28B 3/16; B28B 1/48; B32B 31/16
[52] U.S. Cl. .................. 264/156; 156/252; 156/513; 264/154; 264/163; 425/290; 425/369
[58] Field of Search .................. 264/154, 156, 163; 425/290, 369, DIG. 37; 156/250, 252, 513

[56] References Cited

U.S. PATENT DOCUMENTS

| | | | |
|---|---|---|---|
| 2,633,441 | 3/1953 | Buttress | 425/290 |
| 2,748,863 | 6/1956 | Benton | 264/156 |
| 3,137,893 | 6/1964 | Gelpke | 264/156 |
| 3,403,681 | 10/1968 | Hoey et al. | 604/683 |
| 3,965,906 | 6/1976 | Karami | 604/366 |
| 4,079,739 | 3/1978 | Whitehead | 604/365 |
| 4,128,679 | 12/1978 | Pohland | 156/148 |

FOREIGN PATENT DOCUMENTS

| | | |
|---|---|---|
| 80383 | 1/1983 | European Pat. Off. . |
| 1534042 | 6/1967 | France . |
| 2103933 | 3/1983 | United Kingdom . |
| 2114445 | 8/1983 | United Kingdom . |

*Primary Examiner*—Jan H. Silbaugh
*Assistant Examiner*—Mathieu Vargot
*Attorney, Agent, or Firm*—Thomas J. Connelly

[57] ABSTRACT

A method of perforating a nonwoven web of fibrous fabric by directing the web through a nip defined by first and second moveable members. As the web moves through the nip it is penetrated by a plurality of heated pins projecting from the first member which enter heated apertures formed in the second member. The penetration of the pins causes the fibers of the fabric to separate and enter into the apertures and form openings through the web. The openings are surrounded by dense consolidated rings exhibiting greater hydrophilic properties than the nonperforated surface of the web.

16 Claims, 7 Drawing Sheets

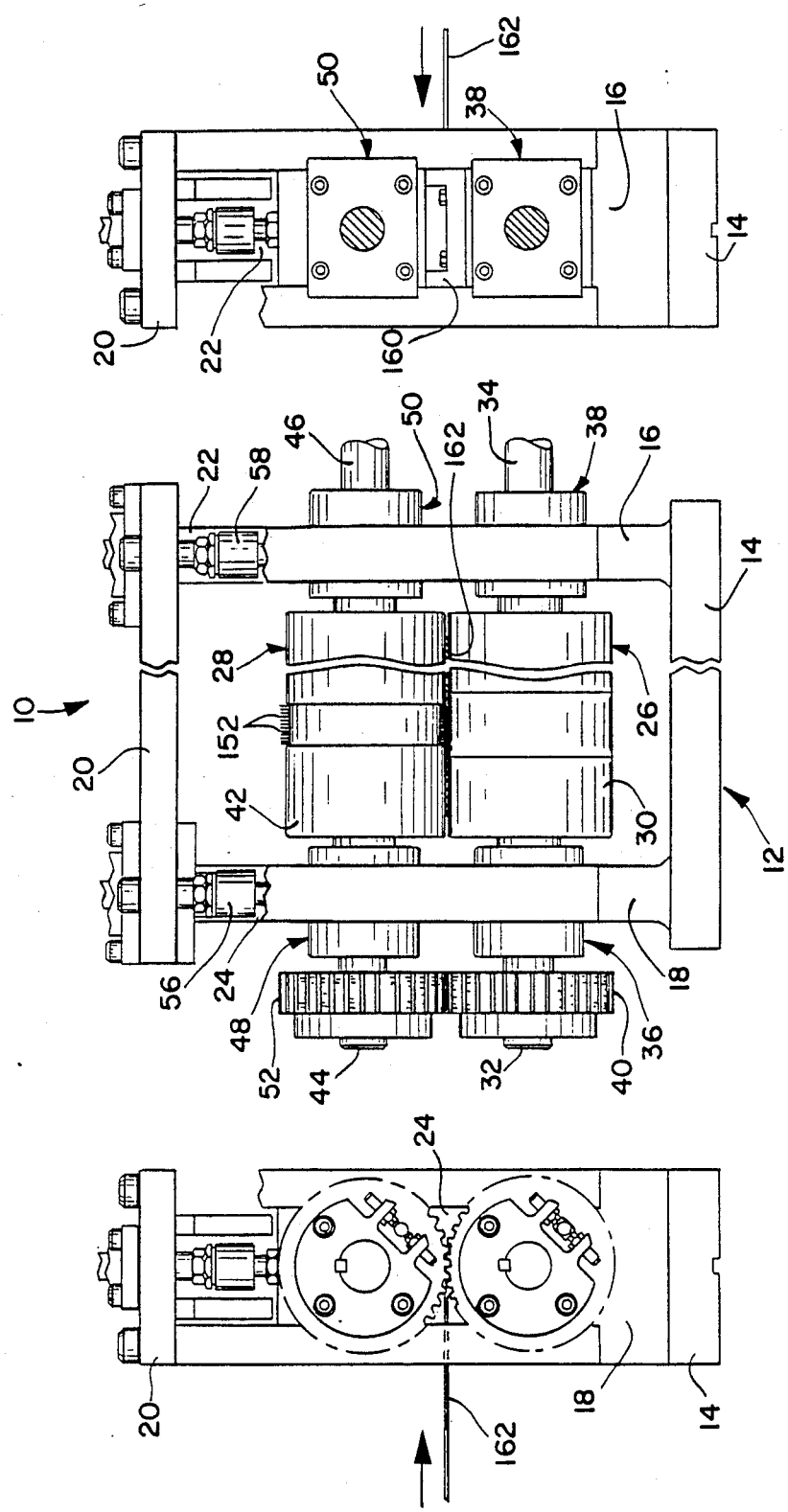

METHOD OF PERFORATING A NONWOVEN WEB AND USE OF THE WEB AS A COVER FOR A FEMININE PAD

This application is a continuation-in-part of Ser. No. 032,154 filed on Mar. 27, 1987, now abandoned, which was a division of Ser. No. 774,252, filed on Sept. 9, 1985, also now abandoned.

FIELD OF THE INVENTION

This invention relates to a method of perforating a nonwoven web and using the web as a cover for a feminine pad. More specifically, this invention relates to a method of perforating a nonwoven web, with a patterned multitude of fine heated pins to form dense consolidated rings and raised ridges about the openings formed in the web.

BACKGROUND OF THE INVENTION

Feminine pads, also referred to as sanitary napkins, such as those described in U.S. Pat Nos. 4,397,644 and 4,079,739, are well known. Sanitary napkins of the prior art are normally of multilayered construction including: a fluid absorbent core interposed within a fluid impermeable baffle and a fluid permeable cover. The cover being designed to transmit menstrual fluid or the like across its boundary to the absorbent core. As those skilled in the art will readily appreciate, the interrelationship of components is substantially more intricate; however, for purposes of basic understanding, the foregoing suffices. Within those very general parameters one may also profitably compare the contoured sanitary napkin disclosed in U.S. Pat. No. 4,184,498.

Conventional sanitary napkins typically comprise an absorbing layer serving as the uppermost layer to be held in contact with the human body and made of a hydrophilic absorbent material such as absorbent paper, absorbent cotton, pulverized pulp or the like, so that when having absorbed therein a large quantity of body fluid, the napkin becomes sticky on its surface. In addition, when the absorbing layer is subjected to pressure, the body fluid once absorbed therein is likely to ooze or flow out reversely toward the body making the surface sticky. Thus, the uppermost layer of the sanitary napkin becomes very uncomfortable to use and unsanitary. This problem is particularly apparent when body fluid is discharged in large quantities within a relatively short period of time in the initial stage of menstruation. The absorbing layer is unable to fully absorb the discharge in some cases, permitting the body fluid to remain on the surface of the absorbing layer and allowing sideways leakage when the layer is subjected to varying body pressures.

Even at times of light flow, however, body fluids do not necessarily readily pass through the fluid permeable cover into the fluid absorbent core of the sanitary napkin. It has been recognized that menses is a complex fluid with uterine blood being only one component of its composition. Menses also contains cellular debris and a mucus-like fraction. The composition of menses has a significant effect on the transport of fluid from the cover into the absorbent matrix of a sanitary napkin, especially for certain women who consistently have high viscosity menses and comparatively low flow volumes. High viscosity menses tends to stay on the upper surface of the cover of the sanitary napkin.

The cover, or top layer of a sanitary napkin is an important structural component respecting overall product efficacy, both objectively and subjectively from the user's point of view. A number of dichotomies become apparent when describing the ideal or preferred top layer of sanitary napkins. For consumer acceptance, a cloth-like texture and feel are preferred. In addition, the top layer should appear clean, dry and stain-free even during use. Thus, the cover layer should remain aesthetically pleasing even during use. Nonwoven webs which most economically and effectively achieve the objective of an acceptable cloth-like texture are, however, generally undesirable when evaluated on their ability to remain clean, dry and stain-free during use. With nonwoven webs, menses tends to get hung up or remain on the top layer while never reaching the lower absorbent layer since the fibers oftentimes act to block the path to the absorbent layer. Thus, the sanitary napkin becomes uncomfortable, wet, sticky and generally unaesthetically pleasing.

SUMMARY OF THE INVENTION

Briefly, this invention relates to a method of perforating a nonwoven web and use of the web as a top layer or cover for a sanitary napkin. The cover has a cloth-like texture or feel but remains clean, dry and relatively stain-free during use, in contra-distinction to conventional fibrous covers. An attribute of the present invention is that the material has the ability to relatively rapidly transfer menses across its boundaries into the absorbent material lying beneath it while preventing the return of that fluid to the cover; i.e., the cover has excellent rewet characteristics. Covers of the foregoing variety are conveniently and beneficially provided in a fairly simple manner using straight-forward apparatus. Thus, capital expense and elaborate methodologies are minimized while nonetheless delivering product of enhanced characteristics as aforesaid. Still further, the cover optionally provides means for improved stain masking, either integrally or in association with the absorbent core or matrix of a sanitary napkin, increasing significantly the aesthetic characteristics of this class of catamenial product.

The foregoing advantage and benefits are achieved by forming a perforated nonwoven web comprising essentially broken thermoplastic fibers wherein the nonwoven web contains distinct, stable perforations with a consolidated zone or area of densified, thermally set material immediately surrounding each such perforation. The fibrous web substrate is most preferably autogenously bonded and thus does not require an ancillary adhesive. When the perforated, selectively or discretely consolidated nonwoven web is adopted as a cover material for a sanitary napkin, the perforations tend to attract body fluid (i.e., menses), and thus allow for relatively easy passage of the fluid through the web into the absorbent area of the napkin.

A novel rotary, perforating apparatus provides the desired apertured nonwoven web system of the present invention. In a particularly preferred aspect thereof, matting pin/hole rolls suitably heated relative to the physical characteristics of the web to be apertured provide an expedient apparatus and convenient method for achieving the ends of the present invention.

Other advantages of the present invention, and a fuller appreciation thereof, will become apparent as the following detailed description ensues.

BRIEF DESCRIPTION OF THE DRAWINGS

This invention can better be understood by references to the drawings in which:

FIG. 1 is a cross-sectional view through the length of the rotary, perforating apparatus of the present invention.

FIG. 2 is a partial cross-sectional view through the drive side of the apparatus shown in FIG. 1.

FIG. 3 is a partial cross-sectional view through the operator side of the apparatus shown in FIG. 1.

DETAILED DESCRIPTION OF THE PREFERRED EMBODIMENT

Figure 4:
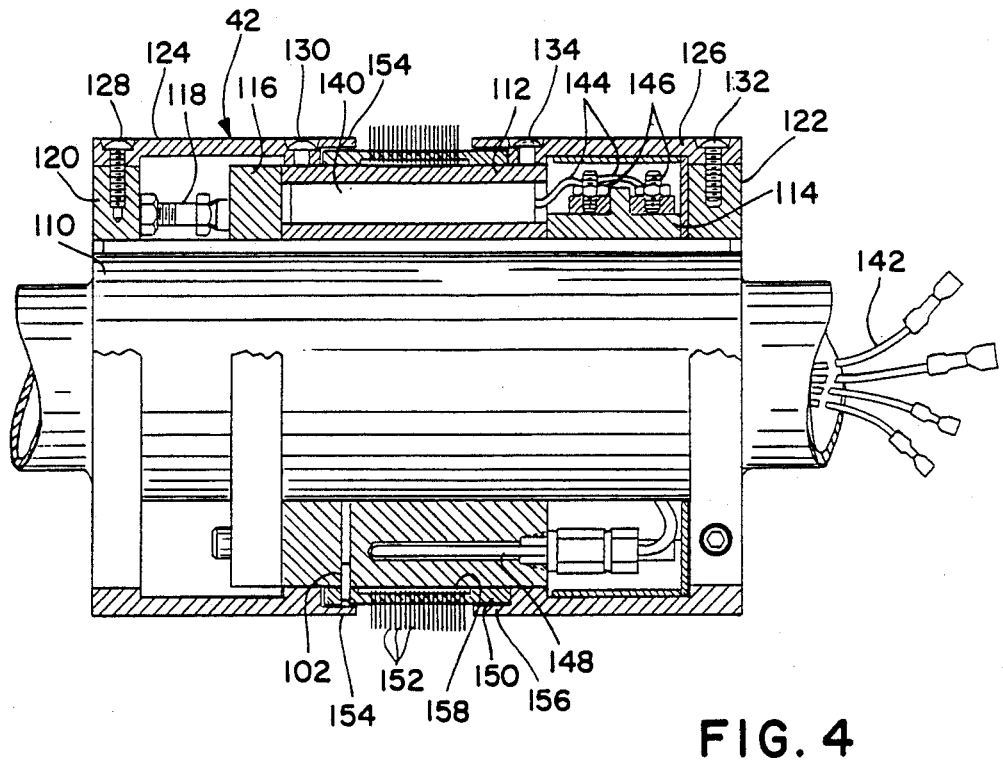
FIG. 4 is a cross-sectional view through the pin roll of the apparatus shown in FIG. 1.

Any type of nonwoven web comprising fusible polymeric filaments is useful in the practice of the present invention. For instance, a suitable nonwoven web cover material is a uniform spunbonded nonwoven web having one and one-half denier or larger filaments. Such a material is described in U.S. Pat. No. 4,340,563, to which reference is made for a fuller description of such material. This material is also referred to as a linear drawn spunbonded (LDS).

Alternatively, a bonded carded web is useful in the practice of the present invention. The bonded carded web is generally composed of 100% polypropylene, however, blends containing rayon, polyester and the like are equally suitable. Hollowfill fiber types may also be present in the bonded carded web. The bonded carded web is generally in the range of about 10 to about 50 gsm (grams per square meter) and is preferably within the range of about 18 to about 24 gsm. The bonded carded web fibers range from about one and one-half to about three denier. The staple length is within the range of about one and one-half to about two inches. Alternatively, the bonded carded web may be laminated to a film of ethyl methacrylate.

Another suitable nonwoven web is a "coform" material as described in U.S. Pat. No. 4,100,324. Coform is a blend of meltblown microfibers and an absorbent fiber such as pulp fluff. Representative meltblown fibers include polypropylene, polyethylene, polyethylene terephthlate, polyamides, acrylic and nylon fibers or blends. Alternatively, the coform may be laminated to a spunbonded nonwoven web.

A sanitary napkin cover such as that described in U.S. Pat. No. 4,397,644, is also useful in the practice of the present invention. The material described therein is primarily a nonwoven thermoplastic web which is of sufficiently open structure to enhance the transfer of menses into an absorbent layer. Bonding is used to accomplish integration. This may be achieved by the application of heat, such as hot calendar embossing, or by ultrasonic means. Alternatively, the bonding may be accomplished by mechanical manipulation of the fibers without heat as, in needling. Ultrasonic bonding is particularly preferred. This nonwoven web is typically comprised of a polyester and polypropylene combination, typically 30% and 70% respectively. Alternatively, it may be comprised of 100% polypropylene. Hollowfill fiber types may also be present. This nonwoven web is a carded web which is generally in the range of about 30 to about 150 gsm. Preferably, this nonwoven web ranges from about 40 to about 120 gsm. This material ranges from about one and one-half to about eight denier and may be of high crimp nature thus giving it greater loft. Preferably, it is within the range of about 3 to 8 denier. The staple length is also within the range of about one and one-half to about three inches. This material may alternatively be laminated to spunbonded web.

In particular, suitable fusible fibers for this invention are; Vinyon, a vinyl chloride/vinyl acetate copolymer sold by Celanese Fiber Division and formerly by Avtex Fibers, Inc., of New York, N.Y.; Eastman 410 amorphous or crystalline polyester fibers sold by Eastman Chemical Products, Inc., a Subsidiary of Eastman Kodak Co., Kingsport, Tenn.; or Chisso ES a bicomponent polypropylene/polyethylene fiber sold by Chisso Ltd., Osaka, Japan, which due to its differential melting point for each component of the fiber, could be used as the only thermoplastic fiber as well as in blends with other fibers.

A cylinder which would simply punch holes through and displace fiber is easily achieved. However, the nonwoven web material typically has a memory and thus a strong tendency to return to is original position and thereby close the hole which was just formed.

It has been found that heating the tips of the pin to heat the nonwoven web during penetration acts to heat the fusible polymeric filaments near the area of the pin hole. The polymeric filaments are heated up to a temperature just below the point of melting and cooled to room temperature after the pin is removed. This produced the consolidated area 168 seen in FIG. 12 and FIG. 13. The consolidated rings 168 preferable have a diameter at least twice the diameter of the apertures formed in the web 162. The fusible thermoplastic fibers used in the nonwoven web are meltable and if sufficient heat and pressure are applied to this nonwoven material select areas will consolidate or tend to melt and lose the fibrous network characteristics of nonwoven materials. Under magnification of 20×, the material appears glassine, almost glass-like in appearance. This consolidated or densified area of the material is now hydrophylic, particularly more hydrophylic than the non-perforated surface of the web, and attracts fluid into the perforation or hole. Of course, it is possible that some areas will actually melt and fuse during the course of the subject operation, but this is deemed to be less desirable in the practice of the present invention.

It is also relevant to note that it is not desirable to simply make a hole that removes or evaporates the material previously in the hole or aperture area and thus leaving a solid clean hole in the fabric. The goal of the present invention is to allow all of the material or nonwoven fabric to remain in the web because it is desirable to create some type of depth to the point of penetration. This depth or three dimensional profile is desirable since it allows a perception of thickness or texture to the nonwoven fabric.

Figure 12:
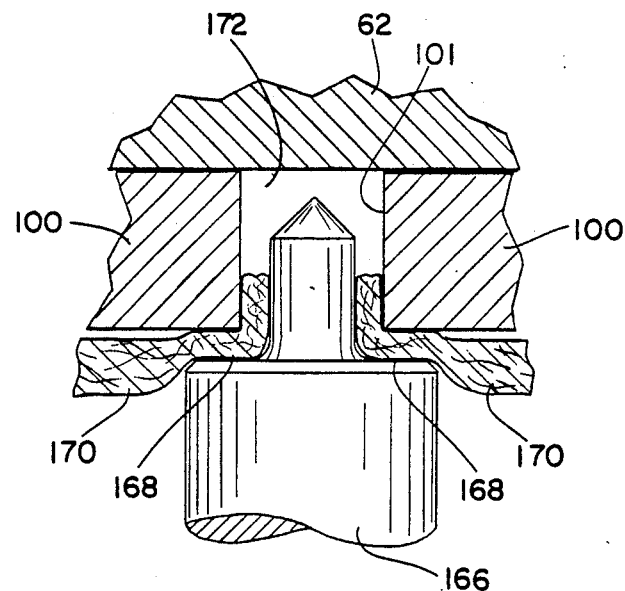
FIG. 12 is a cross-sectional view of a shouldered pin shown to be perforating an area of nonwoven web comprising thermoplastic fibers.
Figure 13:
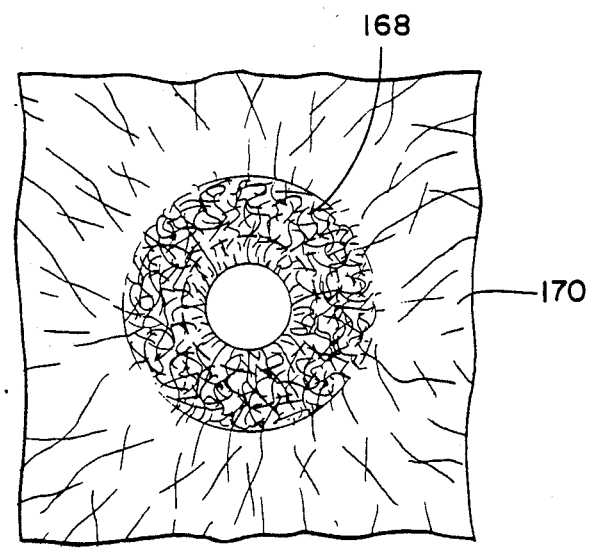
FIG. 13 is a view from the bottom of the nonwoven web of FIG. 12 after the pin has been removed.

Ideally, by making the apertures in the nonwoven web in the manner taught by the present invention, the raised ridges 170 are formed around the periphery of the dense consolidated portions 168 (see FIGS. 12 and 13). The nonwoven material which has not become consolidated or densified is fluffier and thicker and therefore appears like a ridge 170 adjacent the consolidated area 168. This ridged area 170 is ideally considerably less acceptable to fluid or menses since the menses can readily get hung up or stuck on the upper surface of the ridged portion 170 and be unable to enter the absorbent below. Generally, the heavier the fabric, the higher the ridge 170 will be. Advantageously, since the dense consolidated areas 168 are more hydrophylic, the menses will be attracted to these areas and then readily pass through the apertures directly into the absorbent area below.

Preferably, the heated pin makes a distinct, true hole through the nonwoven fabric. That is, no fibers remain in the hole itself. The hole should be free from any extraneous fibers or impurities. If a glob of fluid enters an aperture blocked by a few fibers, the glob of fluid will get hung up on the top of the nonwoven web and remain in that position blocking the entrance of to hole. This is obviously undesirable since it leaves an undesirable stain and wetness on the surface of the nonwoven cover.

The sides of the aperture or perforation formed in the web are preferably at approximately a 90 degree angle with respect to the length of the nonwoven fabric.

Briefly, the apparatus of the present invention may be envisioned as any type of perforating or aperturing device having a first member or containing a series of pins and a second member containing a series of indentions or apertures for receiving entry of the pins. Preferably, the apparatus is a rotary perforating system with the capability of generating a combination of holes having a variety of shapes and in a wide range of patterns with a single pass of the nonwoven web through the system. The rotary perforating/aperturing system can be described as a system comprising two or more cylinders mounted in a configuration such that one or more cylinders are associated with the peripheral surface of a single apertured cylinder.

The apertured cylinder can be described as a hole roll which has been machined or engraved for finished female pattern design. The hole roll is heated internally and the surface is hardened to withstand embossing pressure.

A pin roll is also machined to a finished male pattern design for perforating the web. This matches the hole roll and is equipped with tools, for example, perforating pins, embossing pins or a combination of both. The pin roll is also heated internally.

Referring to FIGS. 1-3, a perforating apparatus 10 is shown having a frame 12 which includes a horizontal base 14, a pair of vertical side walls 16 and 18, and a top member 20 extending across the upper end of the side walls. The side walls 16 and 18 include vertical slots 22 and 24, respectively. Mounted within the slots are a pair of roll assemblies 26 and 28. The lower assembly 26 includes a hollow roll 30 and a pair of support shafts 32 and 34 extending coaxially from opposite ends of the lower roll 30. The shaft 32 is journalled in a bearing mechanism 36 mounted in the slot 24 of the side wall 18. The shaft 32 projects completely through the slot 24 and is operably connected to a toothed gear 40. The other shaft 34 extends completely through the slot 22 and is journalled in bearing housing 38. The shaft 34 is of a hollow construction for the purpose of receiving electrical conduits as will be hereinafter explained.

The upper roll assembly 28 includes a pin roll 42 and a pair of support shafts 44 and 46 extending longitudinally coaxially from opposite ends thereof. The shaft 44 is journalled in a bearing mechanism 48 which is mounted in the slot 24, and the shaft 446 is journalled in a bearing mechanism 50 which is mounted in the slot 22.

The shaft 44 projects completely through the slot 24 and is operably connected to a toothed gear 52 which meshingly engages the gear 40. There is a zero backlash arrangement. The shaft 44 may be driven by a power source (not shown) through a controllable speed variator. The other shaft 46 extends completely through the slot 22 and is hollow in order to receive electrical conduits as will be hereinafter explained.

Referring to FIG. 3, a spacer 160 is shown which is used to adjust the clearance between the rolls 30 and 42. The spacer 160 determines the amount of penetration obtained by the pins into the hole roll 30.

Referring again to FIG. 1, the bearing mechanisms 48 and 50 are each vertically adjustable within the respective slots 24 and 22 by turnbuckle type connectors 56 and 58. The connectors 56 and 58 enable the upper or pin roll 42 to be raised or lowered relative to the hole roll 30 in order to change the vertical depth of the nip defined between the rolls 30 and 42, and also for maintenance and replacement of parts.

Figure 5:
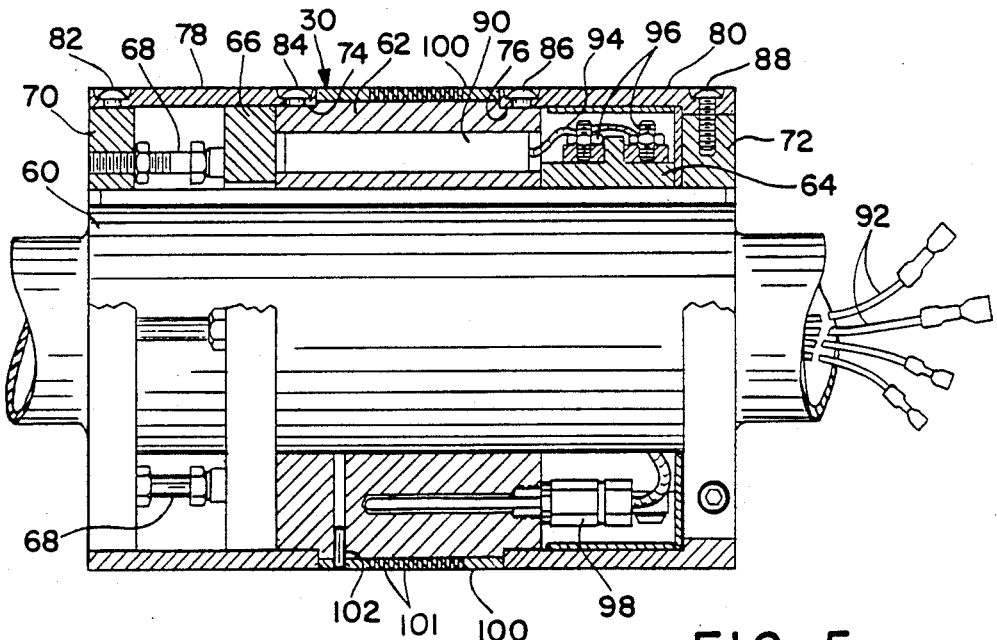
FIG. 5 is a cross-sectional view through the hole roll of the apparatus shown in FIG. 1.
Figure 6:
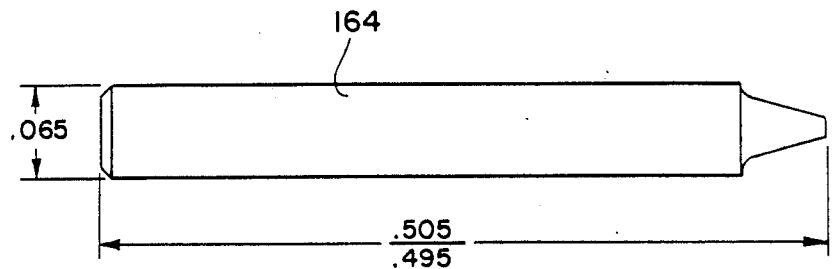
FIG. 6 through FIG. 11 are views of various types of pins which are useful in the practice of the present invention.
Figure 7:
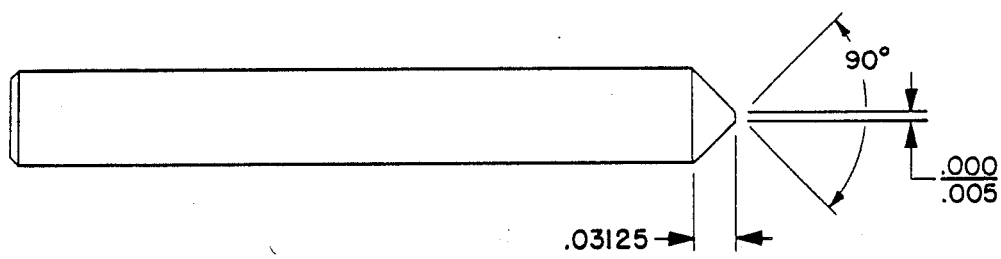
Figure 8:
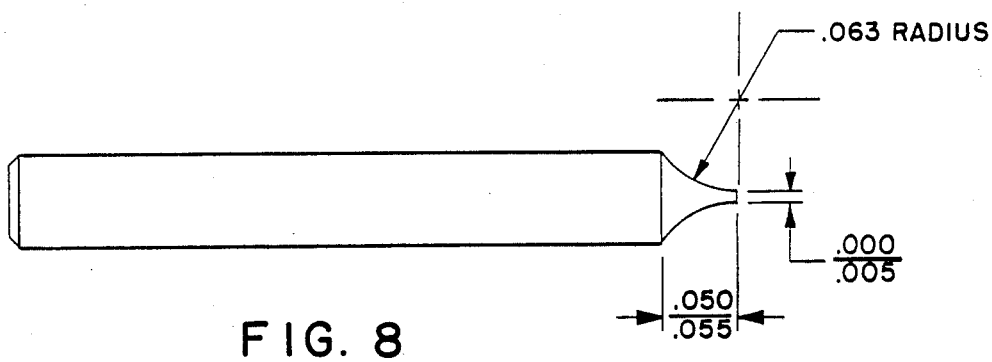
Figure 9:
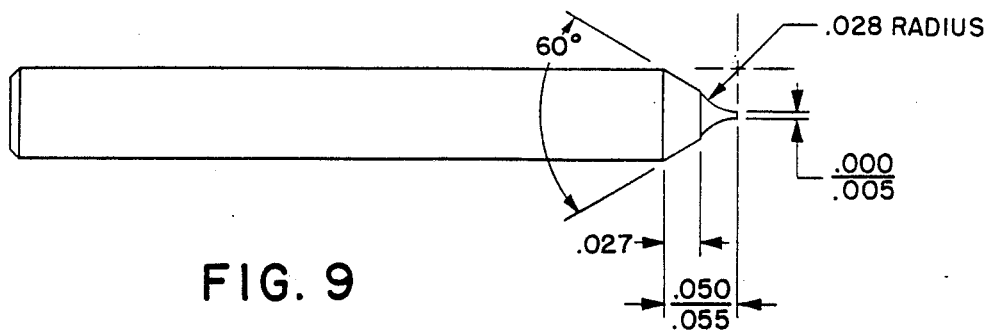
Figure 10:
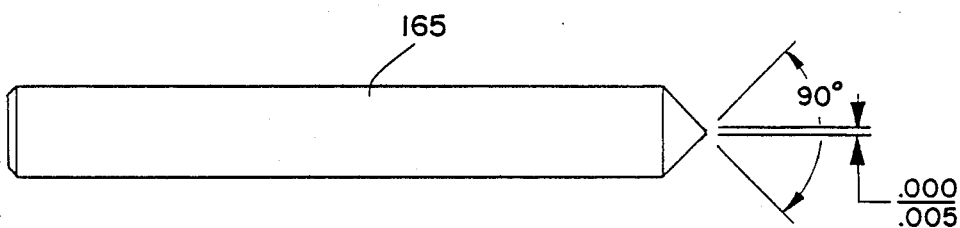

Referring to FIG. 5, the lower or hole roll 30 contains an arbor 60 upon which a sleeve 62 is mounted by a keyway (not shown). The sleeve 62 is formed of a heat conducting material, typically brass, steel or aluminum. Aluminum being preferred. The sleeve 62 is axially sandwiched between a terminal ring 64 and a retaining ring 66. The retaining ring 66 is pushed against the sleeve 62 by turnbuckle type connectors 68 which extend between the retaining ring 66 and an end ring 70. The end ring 70, in turn, is mounted on the arbor 60. The terminal ring 64 is positioned axially between the sleeve 62 and a second end ring 72 which is also mounted on the arbor 60.

The outer periphery of the sleeve 62 is stepped at its ends to define a pair of annular shoulders 74 and 76 which receive the inner ends of a pair of cover rings 78 and 80. A cover ring 78 engages the shoulder 74 and the outer peripheries of both the end ring 70 and the retaining ring 66. The cover ring 78 is suitably fastened to the end ring 70 and to the sleeve 62 by fasteners 82 and 84.

A second cover ring 80 engages the shoulder 76 and the outer periphery of the end ring 72 and is suitably fastened thereto by fasteners 86 and 88.

The sleeve 62 contains a cartridge heater 90 which is electrically connected to an external power source (not shown) via electrical conduits 92 and 94 which are interconnected to terminals 96 carried by the terminal ring 64. The cartridge heater 90 provides heat to the sleeve 62. The sleeve 62 also carries a conventional temperature probe 98 for monitoring the temperature of the sleeve 62.

Mounted on the outside periphery of the sleeve 62 is a cylindrical strip 100. The strip 100 is formed of a heat conducting material such as brass, steel or aluminum. Aluminum being preferred. The strip 100 is mounted on the sleeve 62 by press fit, and a roll pin 102 is inserted through both the strip 100 and the sleeve 62 to prevent relative circumferential movement therebetween. Axial movement of the strip 100 is prevented by the cover sleeves 78 and 80 which bear against the axial ends of the strip 100. The strip 100 contains a series of tiny apertures or sockets 101 arranged in a pre-set pattern for reasons to be explained hereinafter. Preferably, each aperture 101 is round or circular in configuration and is sized to receive a corresponding pin 152 mounted on the upper roll 42.

Referring to FIG. 4, the upper roll 42 contains an arbor 110 upon which a sleeve 112 is mounted in the same manner as the sleeve 62 is mounted on the lower roll 30. The sleeve 112 is formed of a heat conducting material, such as brass, steel or aluminum, and is axially sandwiched between a terminal ring 114 and a retaining ring 116. The retaining ring 116 is pushed against the sleeve 112 by turnbuckle type connectors 118 which extend between the retaining ring 116 and an end ring 120 which is mounted on the arbor 110. The terminal ring 114 is positioned axially between the sleeve 112 and another end ring 122 mounted on the arbor 110.

Extending around opposite ends of the arbor 110 are a pair of cover sleeves 124 and 126. The cover sleeve 124 is secured to the outer peripheries of both the end ring 120 and the sleeve 112 by fasteners 128 and 130. The cover sleeve 126 is secured to the outer peripheries of both the end ring 122 and the sleeve 112 by fasteners 132 and 134.

The sleeve 112 contains a cartridge heater 140 which is electrically connected to an external power source (not shown) via electrical conduits 142 and 144. The conduits 142 and 144 are interconnected to terminals 146 carried by the terminal ring 114. The cartridge heater 140 provides heat to the sleeve 112. The sleeve 112 also caries a conventional temperature probe 148 for monitoring the temperature of the sleeve 112.

Mounted on the outside periphery of the sleeve 112 is a cylindrical strip 150 formed of a heat conducting material such as brass, steel or aluminum. Aluminum being preferred. The strip 150 is mounted on the sleeve 112 by press fit, and a roll pin 102 is inserted through both the strip 150 and the sleeve 112 to prevent relative circumferential movement therebetween. Lip portions 154 and 156 of the cover sleeves 124 and 126 overlie the edges of the strip 150 to aid in the retention thereof.

The strip 150 carries a plurality of needles or pins 152 which project outwardly beyond the outer peripheries of the cover sleeves 124 and 126 by a distance greater than the depth of the nip between the rolls 30 and 42 so that the ends of the pins 152 enter the apertures 101 formed in the lower roll 30. To that end, the apertures 101 are arranged in register with the pins 152 and have a wider diameter than the pins 152 to prevent the pins 152 from contacting the walls of the apertures 101. It will be appreciated from the foregoing that the upper roll 42 may be designated as a pin roll, and the lower roll 30 as a hole roll. Preferably, the pins 152 are formed of a heat conductive material such as brass or steel. The pins 152 are mounted within the strip 150 by placement either from the inside of or from the outside of the cylinder. Placement of the pins 152 on the outside of the cylinder generally requires a space for setting of the pins 152 and the use of a type of compound that upon filling the space provides an element of permanence to the setting, thereby not allowing the pins 152 to be removed. The strip 150 includes a recess 158 facing the sleeve 112 to receive the inner ends of the pins 152. The pins 152 project in radial outward directions with respect to the axis of rotation of the pin roll 42. The apertures 101 formed in the strip 100 project in corresponding directions so as to be able to receive the ends of the pins 152.

It will be appreciated that the pins 152 are heated by conduction due to contact between the heated sleeve 112 and the strip 150 and between the strip 150 and the inner ends of the pins 152. The corresponding hole roll 30 is heated in a similar manner. In operation, the rolls 30 and 42 are synchronously rotated while a web 162 of fabric is fed through the nip defined by the rolls. As this occurs, the pins 152 contact and completely penetrate the fabric, separating the individual fibers to form a generally cylindrical hole through the fabric. Since the pins 156 are heated, the fibers which are displace by each heated pin will be consolidated, compressed or otherwise densified and set in that glassine-line configuration so that the hole cannot reclose. Thus, the fibrous web is autogenously bonded, that is, does not require the use of an adhesive to form structurally stable apertures. Some portion of the fibers being pushed will enter the associated opening in the hole roll 30, whereby dense consolidated rings 168 and annular ridge 170 will be formed around each of the holes. Such dense consolidated rings 168 and raised ridges 170 serve to add depth to the web and thereby improve the cloth-like texture and feel.

Since the pins 152 pass completely through the fabric and tend to set thermally any fiber with which they come into contact, it is assured that all of the holes will be unblocked, i.e., no fiber strands will remain which might extend across, and partially obstruct, the holes.

Nonwoven web fabric 162 may enter the apparatus 10 from either side of the two cylinders.

The foregoing describes a two cylinder configuration with a female patterned main cylinder and a male patterned worker cylinder. However, other embodiments are anticipated such as a three cylinder configuration where the three cylinders may or may not relate in a linear fashion. By using a multiple cylinder configuration a wider variety of patterns can be attained since different male or pin rolls 42 may be used. That is, the pin rolls 42 need not be of the same shape or diameter. This is best depicted in FIGS. 14, 14A, 14B and 14C wherein there are three different pin rolls 42.

At the outset, it is relevant to note that the temperature of the heated pin roll 42 may be higher than that of the hole roll 30 without departing from the spirit of the present invention. This is because approximately 10% of the heat from the pin roll 42 may be lost at the tips of the pins 152, but without a loss in overall operating or functional efficiency. Of course, the two rolls 30 and 42 may be maintained at about the same temperature. There is no easy means of actually heating the tips of the pins 152 thus it is necessary to heat the pin roll 42 itself and via conduction drive heat to the pin head to perform the aperturing operation of the present invention. The temperature of the pin roll 42 may generally be maintained in the range of about 110 degrees Fahrenheit to about 300 degrees Fahrenheit. The hole roll 30, on the other hand, may generally fall within the temperature range of about 90 degrees Fahrenheit to about 350 degrees Fahrenheit.

The speed of the rotary apparatus is generally within the range of about 12 feet on nonwoven fiber per minute to about 220 feet per minute. Since we are dealing with a rotary process, if parameters such as heat, angle of approach of the pin, and the like are controlled, speeds up to approximately 500 feet per minute could conceivably be achieved.

It may be considered suitable to thermally treat the nonwoven web 162 prior to processing. The web 162 may be pre-cooled or postcooled, that is, cooled after undergoing the perforation operation.

Generally, if the speed of a nonwoven web 162 through the rotary apparatus is increased, the temperature must also be increased. These two parameters are directly related since the web 162 may actually burn if the temperature is too high and the pins 152 and the web 162 maintain contact for too long. Preferably, an electrical mechanism is used which is able to maintain both parameters of temperature an speed in the ideal or best relationship.

It is also particularly relevant to note that during the rotary operation, the pins 152 never touch the interior of the corresponding hole on the hole roll 30. The individual hole diameters in the hole roll 30 are most preferably always approximately 0.010 inch larger than the diameter of the pin shaft. This is area 172 in FIG. 12. At a minimum, the hole diameter is selected to be nonbinding respecting the size of the mating pin, typically at least 0.005 inch greater than the diameter of the pin shaft on the pin roll. This spacing is important in the practice of the present invention in order to achieve the proper depth of the entry of the pin through the nonwoven web fabric. Otherwise, if the pin head was too long, it might touch the sides of the hole.

FIG. 6 through FIG. 11 each depict a pin of varying sizes and shapes. Each of these pins are suitable for forming the apertures in the nonwoven web 162. Each pin may be located on a flat plate type device placed on some type of rotary cylinder as was previously described. The hole in the hole roll 30 need not be of the same shape as the pin or pin head. As long as the proper relative dimensions are maintained to preclude binding or interference, the hole may be less defined or more rounded than the pin shape.

Figure 11:
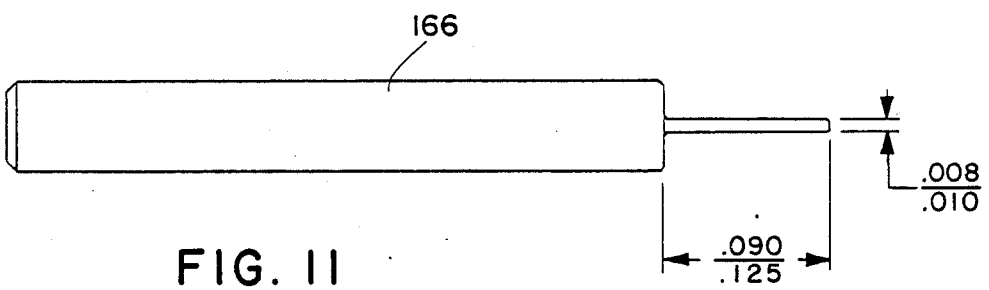
Figure 14:
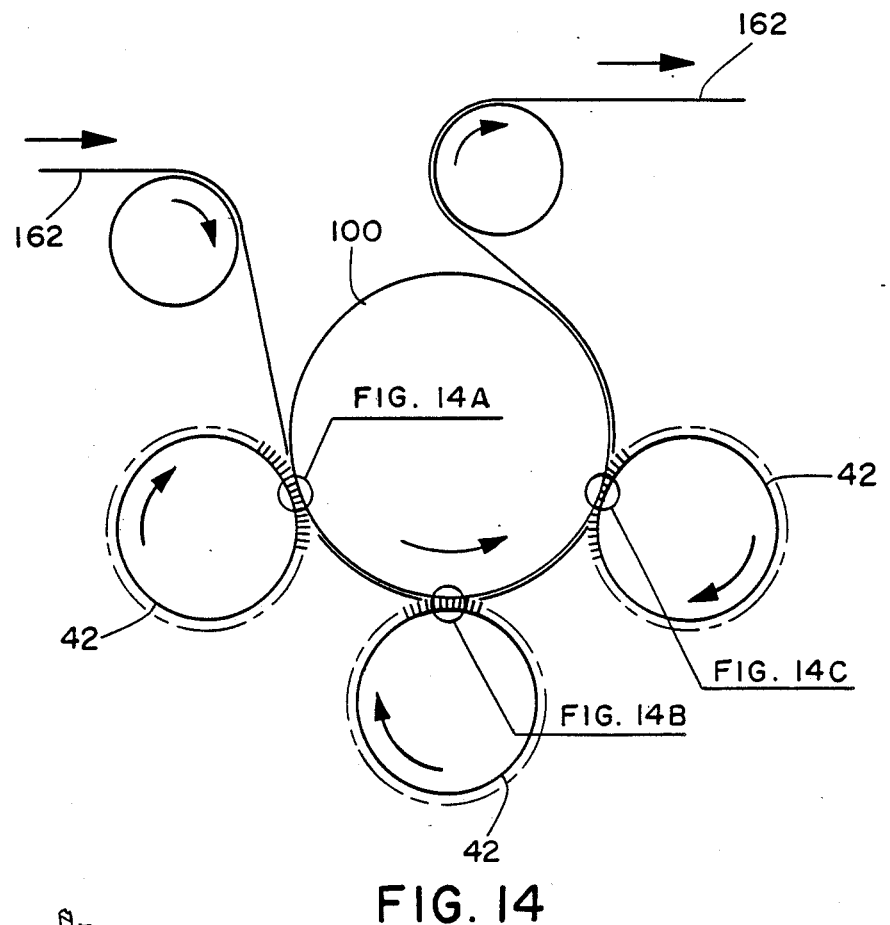
FIG. 14 is a cross-sectional view through the hole roll and each of the pin rolls is a multi-roll system showing the path of the nonwoven web.
Figure 14A:
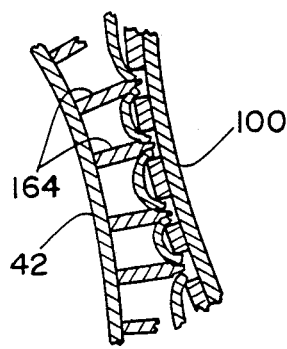
FIG. 14A is an enlarged view of a portion of FIG. 14 showing pins having a profile as depicted in FIG. 6 piercing the nonwoven web and entering into the apertures formed in the roll 100.
Figure 14B:
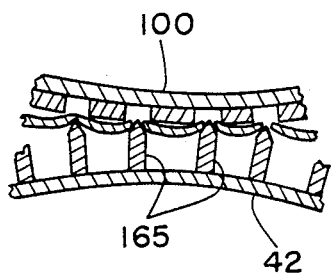
FIG. 14B is an enlarged view of a portion of FIG. 14 showing pins having a profile as depicted in FIG. 10 piercing the nonwoven web and entering into the apertures formed in the roll 100.
Figure 14C:
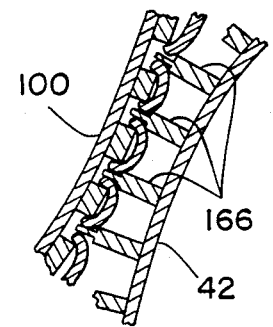
FIG. 14C is an enlarged view of a portion of FIG. 14 showing pins having a profile as depicted in FIG. 11 piercing the nonwoven web and entering into the apertures formed in the roll 100.

FIGS. 11, 12 and 14C depict a shouldered pin 166 which is a suitable pin in the practice of the present invention.

The exact shape and dimensions of the pin head are not critical for present purposes. However, the diameter of the shaft 164 of the pin is important. The shaft 164 of the pin is most relevant since it determines the diameter of the aperture which is formed. Generally, the diameter of the shaft of the pin ranges from about 0.015 to about 0.125 of an inch. Preferably the pin shaft ranges from about 0.032 to about 0.097 of an inch. The pins essentially act to burst the nonwoven fabric while not actually damaging or breaking any of the fibers themselves.

The pin itself is comprised of a metal. Preferred metals include steel or brass with steel being more preferred. Any type of steel is suitable in the practice of the present invention including hard or soft steel such as stainless steel. The preferred metal is one which would allow the greatest heat transfer from the heated roll to the pin head.

A plastic pin or pin head may be desired in the practice of the present invention at the option of the designer. However, some plastics are generally not able to withstand the high operating temperatures as described herein and materials selection needs to be made accordingly.

Alternatively, the pin may comprise a metal core such as steel with a plastic surface. The plastic covering may be applied by coating or it may be mechanically fit by pushing the coat or layer onto the pin. The plastic coated metal pin concept is particularly advantageous since the plastic surface provides a smooth, slippery surface to the pin thus allowing it to penetrate the nonwoven fabric more readily. A preferred coating material would be a fluoropolymer coating, in particular, polytetrafluoroethylene (Teflon ® by Dupont).

A metal pin may also be impregnated with plastic material. In this case, the metal surface must be porous enough to allow the actual impregnation of the plastic onto the metal. Suitable plastic materials for this impregnation include, but are not limited to, polypropylene, polyethylene and the like.

Every one of the pins must enter the matching hole on the hole roll 30 with perfect clearance. There is never any metal-to-metal, or in the case of plastic coated pins, plastic-to-plastic contact.

The diameter of the shaft of the pin is generally in the range of 0.015 inch to about 0.125 inch. This is the true diameter of the tool therefore this value does not necessarily represent the diameter of the finished hole. The finished hole may be slightly oblong and slightly larger than the diameter of the pin shaft when completed. The exact diameter of the hole is dependent on a variety of factors that must be each independently determined.

In determining the number of holes per area on the nonwoven web 162, it is pertinent to discuss the percent of openness, as that is a more meaningful value than the pin population per square inch since pin diameter varies so widely. The goal is to open and texturize the surface of the nonwoven to allow fluid menses to penetrate more readily while at the same time to minimize rewet, that is, a return of the fluid to the nonwoven cover. Maintaining a product which is aesthetically pleasing is thus a key to the present invention.

The degree of openness or perforation on the nonwoven web can range from about 20% to about 55% of the available surface area. The upper practical limit seems to be approximately 55% due to mechanical/physical limitations of the system. Preferably, the degree of openness is in the range of about 40% to about 50%.

The pattern of the pins themselves may vary considerably. If a smaller shaft size is selected, a greater number of holes are necessary to achieve the same degree of openness.

It is also suggested to add a binder to the intact area of the nonwoven web, that is, the area between the holes or apertures. This has been described as the ridge area. The addition of a binder has two-fold advantage. First, the binder will not destroy the cloth-like texture and appearance of the nonwoven web. Second, by filling in the tiny voids within the ridges, fluid will not have a tendency to get hung up there and therefore alter the visual appearance of the surface of the sanitary napkin. The binder maybe applied at any stage of the process such as during the formation of the nonwoven web, sprayed on after the web is formed or added during the aperturing or consolidating process. The optimal qualities of a binder is that it withstand body temperature heat, but neither melt nor rub off. Suitable binders include polyethylene glycol and the like.

Another feature of the subject invention involves color toning or pigmenting either the area of the aperturing or the entire top surface of the sanitary napkin which may or may not contain the apertures of the present invention. This color toning or pigmenting of the cover layer has several advantages. Most significantly, it tends to affect perceptual or visual masking of fluid during use of the sanitary napkin. The coloring may thus attenuate the typical red menstrual stain observable during use. It also improves visual perception by emphasizing in the case of a perforated nonwoven cover material that the product is effective in achieving a degree of physical separation between the body of the wearer and the core containing or laden with menstrual fluid. The perforations also become more distinct and noticeable. The coloring of pigmenting is selective and may involve all or a portion of the nonwoven cover material. The preferred colors include those in the blue, blue-green, and green areas of the visual light spectrum. Alternatively, the toning or coloring agent may be already present in the binder. In addition, instead of toning or pigmenting the cover layer itself, a similar effect could be achieved by toning or pigmenting the absorbent material directly under the cover layer. If a more conventional white coloration is desired a whitening or opacifying agent maybe used such as titanium dioxide ($TiO_2$) up to a level of approximately 8% of the total weight of the cover material.

As previously indicated, the apertured nonwoven web 162 is suitable as the uppermost layer or cover of a feminine pad. The raised ridges 170, as shown in FIG. 12, face the perineal area of the wearer when the nonwoven web is used as a cover on a feminine sanitary napkin. Any sanitary napkin bearing a fibrous cover currently known in the art may contain the apertured nonwoven web cover material of the present invention. In the simplest terms, a feminine sanitary napkin is comprised of a highly absorbent core of fibrous material or the like, a fluid pervious cover member such as that described by the present invention and a fluid impervious backing member which is oftentimes referred to as a baffle, with pressure sensitive attachment means disposed thereon. The highly absorbent core of fibrous material may comprise any of the well-known materials currently known in the art, including wood pulp fluff, multiple layers of cellulose wadding, cotton or rayon fibers, cellulose sponge, hydrophilic synthetic sponge, and the like.

The fluid impervious backing member or baffle is preferably a thin plastic film such as polyethylene or polypropylene of about one-half to three mils (i.e., thousandth of inches) in thickness. Other thin flexible films such as polyvinylchloride, polyvinylidene chloride, natural rubber, etc., may be employed. Another useful material is a thin polyurethane film which maybe of open or close-celled construction on the interior, and may be absorbent or nonabsorbent, but which should have a closed fluid-impervious skin on at least the bottom surface.

Exemplary of such a baffle is a conventional 0.4 oz. per square yard spunbonded web with a 0.75 mil (0.00075 inch) film of an ethylene methyl acrylate (EMA), preferably with the EMA side toward the body of the absorbent material.

According to this invention, the sanitary napkin is provided with improved comfort and the ability to relatively rapidly transfer viscous menses from the apertured nonwoven web cover material into the absorbent layer below. The absorbent matrix described in U.S. Pat. No. 4,397,644 contains a principal absorbent component characterized by relatively high fluid retention and a second component including comfort enhancement capabilities positioned at least in part between the principal absorbent and the fluid permeable cover or wrap. The second component, that is the comfort enhancing component, may be integrated with the apertured nonwoven web cover material of the present invention to provide intimate contact and densification of localized regions. As a consequence, fluid transfer routes are established and fluid is conveyed to the principal absorbent component. This fluid transfer system may be used in association with the nonwoven web cover of the present invention.

Figure 15:
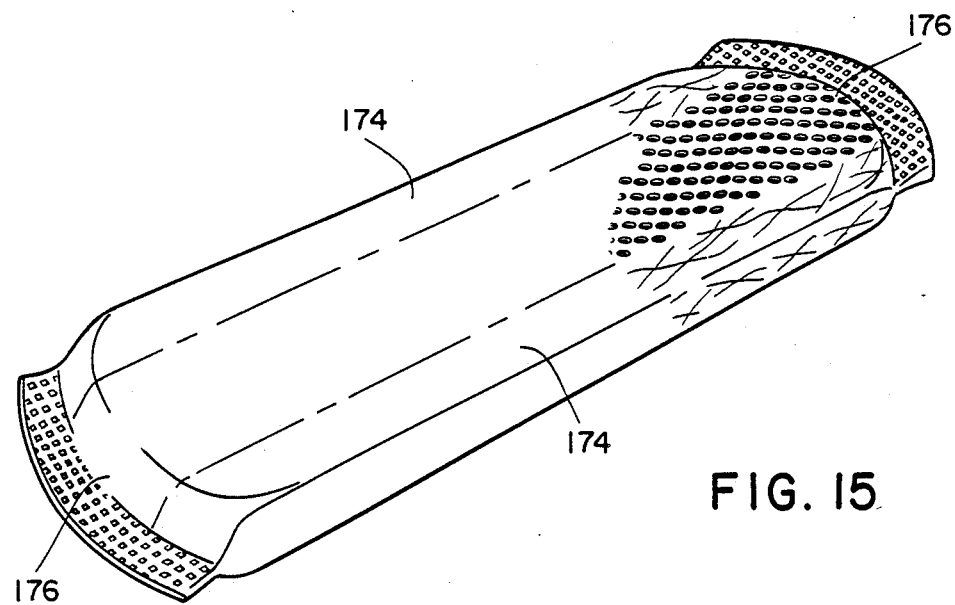
FIG. 15 is a plan view of the top or cover layer of a feminine sanitary napkin depicting the pattern of the perforations.
Figure 16:
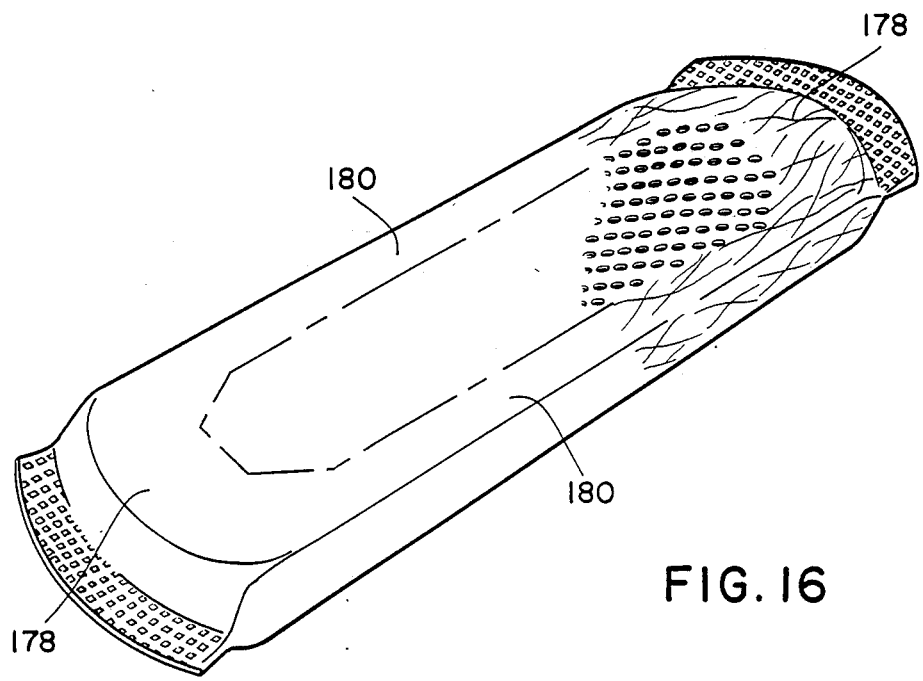
FIG. 16 is a plan view of the top or cover layer of another feminine sanitary napkin depicting the pattern of the perforations.

FIGS. 15 and FIG. 16 indicate two possible designs or patterns for the apertured holes on the surface of the cover material of the sanitary napkin. Looking at the length of the sanitary napkin, the range of the width of the apertured material is generally from about one to about two inches wide, that is, the apertures do not extend the full width of the sanitary napkin. This can be observed at areas 174 and 180 of FIG. 16. The area without aperturing is generally about 0.75 inch to about 2.0 inch wide on each side of the sanitary napkin.

Alternatively, a distinct registered pattern may be obtained on the sanitary napkin cover. That is, the apertured pattern of approximately one to two inches wide need not extend the full longitudinal length 178 of the sanitary napkin as described in FIG. 16. Typically, the aperturing may be terminated from ¾ inch to approximately 2 inches from the longitudinal edge of the pad. In the case of the registered pattern the apertured portions of the cover material does not touch the edges of the sanitary napkin and is primarily located in and near the center of the sanitary napkin. This is obviously most advantageous since it corresponds with the perineal area of the wearer. In FIG. 15, the aperturing 176 extends the full longitudinal length of the sanitary napkin.

While the invention has been described in connection with a specific embodiment, it will be understood that is not intended to limit the invention to those embodiments. On the contrary, it is intended to cover all alternatives, modifications, and equivalents as may be included within the spirit and scope of the invention as defined by the appended claims.

We claim:

1. A method of perforating a nonwoven web of fibrous fabric comprising the steps of:
   (a) directing said web through a nip defined by first and second movable members; and
   (b) penetrating said web with a plurality of heated pins each having a shoulder which surrounds a penetrating point, said pins projecting outward from said first member and entering heated apertures formed in said second member causing fibers of said fabric to separate and enter into said apertures to form openings through said web, each of said shoulders having a diameter larger than the diameter of a corresponding aperture into which said point enters, each of said openings being surrounded by a consolidated ring formed by pressing said web between one of said heated pins and a corresponding aperture and between one of said shoulders and said second member, a combination of said openings and said consolidated rings exhibiting greater hydrophilic properties than the non-perforated surface of said web.

2. The method of claim 1 wherein said first movable member is heated to a temperature of between about 100 degrees Fahrenheit to 300 degrees Fahrenheit.

3. The method of claim 1 wherein said second movable member is heated to a temperature of between about 90 degrees Fahrenheit to 350 degrees Fahrenheit.

4. A method of forming a perforated liquid permeable nonwoven cover material for a feminine pad, said pad including a fluid absorbent partly covered by said cover material and partly surrounded by a baffle which in turn is bonded to said cover material, said method comprising the steps of:
(a) directing said cover material through a nip defined by first and second movable members; and
(b) penetrating said cover material with a plurality of heated pins each having a shoulder which surrounds a penetrating point, said pins projecting outward from said first member and entering heated apertures formed in said second member causing fibers of said cover material to separate and enter into said apertures to form openings through said cover material, each of said shoulders having a diameter larger than the diameter of a corresponding aperture into which said point enters, each of said openings being surrounded by a consolidated ring formed by pressing said cover material between one of said heated pins and a corresponding aperture and between one of said shoulders and said second member, a combination of said openings and said consolidated rings exhibiting greater hydrophilic properties than the non-perforated surface of said cover material.

5. A method of perforating a nonwoven web of fabric including fusible polymeric filaments, said method comprising the steps of:
(a) positioning a first roll relative to a second roll to obtain a preselected nip opening therebetween, said first roll containing a plurality of radially extending pins each having a shoulder which surrounds a penetrating point, and said second roll containing a plurality of circular apertures arranged and sized to receive said pins each of said shoulders having a diameter larger than the diameter of a corresponding aperture into which said point enters
(b) heating both said first and second rolls to a predetermined temperature;
(c) directing said web between said nip; and
(d) rotating said first and second rolls to cause said pins to penetrate said web and enter into said apertures, said penetration causing fibers of said fabric to separate and be drawn into said apertures to form openings in said web which are surrounded by consolidated rings formed by pressing said web between one of said heated pins and a corresponding aperture and between one of said shoulders and said second roll, a combination of said openings and said consolidated rings, said rings imparting a three dimensional profile to said web which facilitates passage of fluid through said openings.

6. The method of claim 5 wherein said first roll is heated to a temperature of between about 110 degrees Fahrenheit to 300 degrees Fahrenheit.

7. The method of claim 5 wherein said second roll is heated to a temperature of between about 90 degrees Fahrenheit to 350 degrees Fahrenheit.

8. The method of claim 5 wherein said web is cooled after being perforated.

9. The method of claim 5 wherein said web is pre-cooled prior to being perforated.

10. A method of perforating a nonwoven web of fibrous fabric comprising the steps of:
(a) positioning a first roll relative to a second roll to obtain a preselected nip opening therebetween, said first roll containing a plurality of radially extending pins each having a shoulder which surrounds a penetrating point, and said second roll containing a plurality of circular apertures arranged and sized to receive said pins each of said shoulders having a diameter larger than the diameter of a corresponding aperture into which said point enters;
(b) heating both said first and second rolls to a predetermined temperature;
(c) directing said web between said nip; and
(d) rotating said first and second rolls to cause said pins to penetrate said web and enter into said apertures, said penetration causing fibers of said fabric to separate and be drawn into said apertures to form openings in said web which are surrounded by consolidated rings formed by pressing said web between one of said heated pins and a corresponding aperture and between one of said shoulders and said second roll, a combination of said openings and said consolidated rings exhibiting greater hydrophilic properties than the non-perforated surface of said web.

11. The method of claim 10 wherein said first roll is heated to a temperature of between about 110 degrees Fahrenheit to 300 degrees Fahrenheit.

12. The method of claim 10 wherein said second roll is heated to a temperature of between about 90 degrees Fahrenheit to 350 degrees Fahrenheit.

13. The method of claim 10 wherein said web is cooled after being perforated.

14. The method of claim 10 wherein said web is pre-cooled prior to being perforated.

15. A method of forming a perforated nonwoven cover material for a feminine pad, said pad including a fluid absorbent having a first surface facing the body of a user which is covered by said cover material and a liquid impermeable baffle surrounding the remaining portion of said absorbent and which is bonded to said cover material, said method comprising the steps of:
(a) positioning a first roll relative to a second roll to obtain a preselected nip opening therebetween, said first roll containing a plurality of radially extending pins each having a shoulder which surrounds a penetrating point, and said second roll containing a plurality of circular apertures, arranged and sized to receive said pins, each of said shoulders having a diameter larger than the diameter of a corresponding aperture into which said point enters;
(b) heating both said first and second rolls to a predetermined temperature;
(c) directing said cover material between said nip; and (d) rotating said first and second rolls to cause said pins to penetrate said cover material and enter into said apertures, said penetration causing fibers of said cover material to separate and be drawn into said apertures to form openings therein which are surrounded by consolidated rings formed by pressing said cover material between one of said heated pins and a corresponding aperture and between one of said shoulders and said second roll, a combination of said openings and said consolidated rings, exhibiting a greater hydrophilic property than the non-perforated surface of said cover material.

16. A method of perforating a nonwoven web of fabric comprising the steps of:
(a) directing said web through a nip defined by first and second movable members; and
(b) penetrating said web with a plurality of heated pins each having a shoulder which surrounds a penetrating point, said pins projecting outward from said first member and entering heated apertures formed in said second member causing fibers of said fabric to separate and enter into said apertures and form openings through said web which occupy approximately 20 to 55% of the available surface area of said web each of said shoulders having a diameter larger than the diameter of a corresponding aperture into which said point enters, each of said openings being surrounded by a consolidated ring formed by pressing said web between one of said heated pins and a corresponding aperture and between one of said shoulders and said second member, a combination of said openings and said consolidated rings exhibiting greater hydrophilic properties than the non-perforated surface of said web.

* * * * *